US007863588B2

(12) United States Patent
Hirono

(10) Patent No.: US 7,863,588 B2
(45) Date of Patent: Jan. 4, 2011

(54) LIGHTING OPTICAL APPARATUS AND SAMPLE INSPECTION APPARATUS

(75) Inventor: Masatoshi Hirono, Kanagawa (JP)

(73) Assignees: Kabushiki Kaisha Toshiba, Tokyo (JP); NEC Corporation, Tokyo (JP)

( * ) Notice: Subject to any disclaimer, the term of this patent is extended or adjusted under 35 U.S.C. 154(b) by 392 days.

(21) Appl. No.: 12/047,759

(22) Filed: Mar. 13, 2008

(65) Prior Publication Data

US 2008/0237489 A1 Oct. 2, 2008

(30) Foreign Application Priority Data

Mar. 30, 2007 (JP) ............................ 2007-090423

(51) Int. Cl.
*G01J 1/00* (2006.01)

(52) U.S. Cl. .............................. 250/504 R; 250/492.1; 362/268; 362/331; 359/362; 359/368; 359/385; 359/710

(58) Field of Classification Search ............ 250/504 R, 250/492.1; 362/268, 331; 359/362, 368, 359/385, 710
See application file for complete search history.

(56) References Cited

U.S. PATENT DOCUMENTS 4,682,885 A * 7/1987 Torigoe ...................... 355/67
6,243,206 B1 * 6/2001 Wangler .................... 359/621
6,913,373 B2 * 7/2005 Tanaka et al. .............. 362/268
7,242,457 B2 * 7/2007 Shinoda ...................... 355/67
7,532,406 B2 * 5/2009 Hill et al. ................... 359/623
2002/0176255 A1 * 11/2002 Yamauchi et al. .......... 362/299
2003/0020904 A1 * 1/2003 Uto et al. ................ 356/237.2

FOREIGN PATENT DOCUMENTS

| | | | |
|---|---|---|---|
| JP | 2003-42967 | | 2/2003 |
| JP | 2003-329610 | | 11/2003 |
| JP | 2006-98156 | | 4/2006 |
| JP | 200698156 | A * | 4/2006 |

* cited by examiner

*Primary Examiner*—Jack I Berman
*Assistant Examiner*—Michael Maskell
(74) *Attorney, Agent, or Firm*—Oblon, Spivak, McClelland, Maier & Neustadt, L.L.P.

(57) ABSTRACT

A lighting optical apparatus using a deep ultraviolet light source that are easy to adjust due to a configuration with fewer components, has high illuminant and illuminant uniformity on an irradiated surface are provided. The apparatus has a deep ultraviolet light source from which deep ultraviolet rays are emitted, a first double-sided cylindrical lens which has a cylindrical lens array on both sides with a configuration of cylinder axes intersecting at right angles, a second double-sided cylindrical lens which has a cylindrical lens array on both sides with a configuration of cylinder axes intersecting at right angles, and a condenser lens.

5 Claims, 4 Drawing Sheets

FIG.1A XZ plane
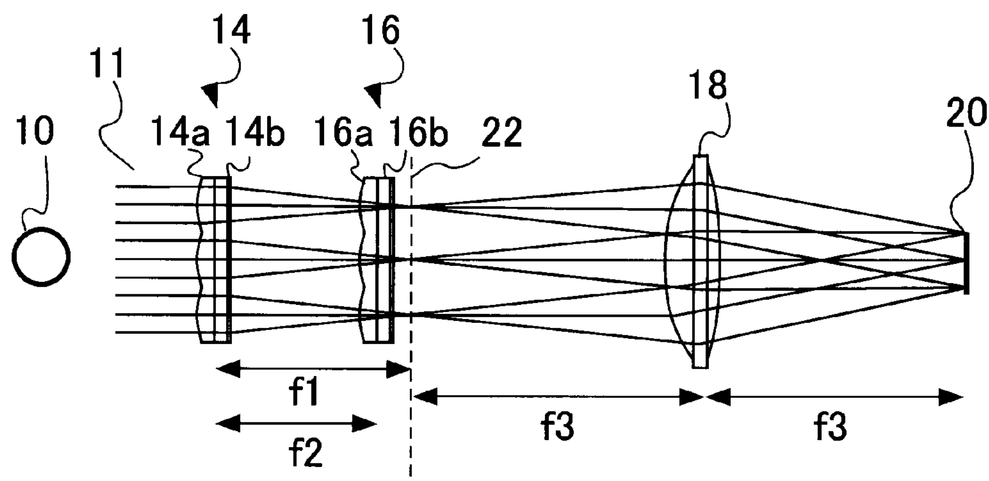
FIG.1B YZ plane
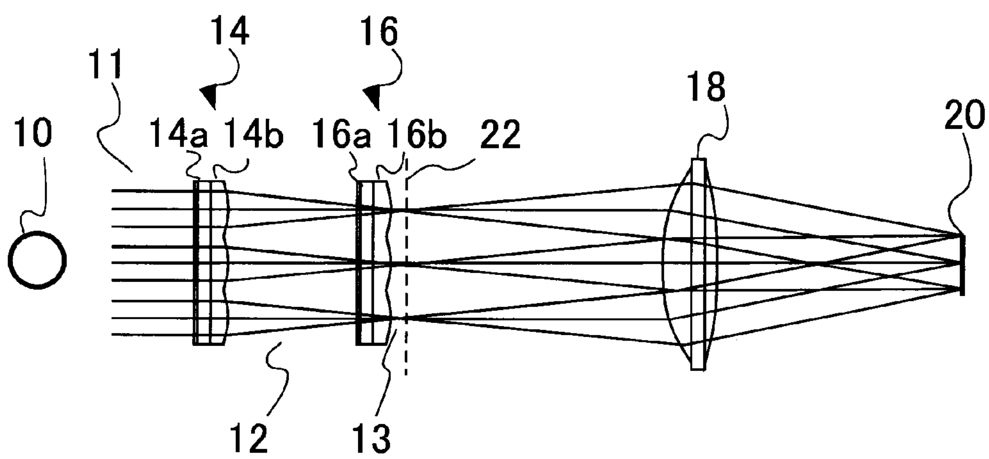

FIG.2A XZ plane
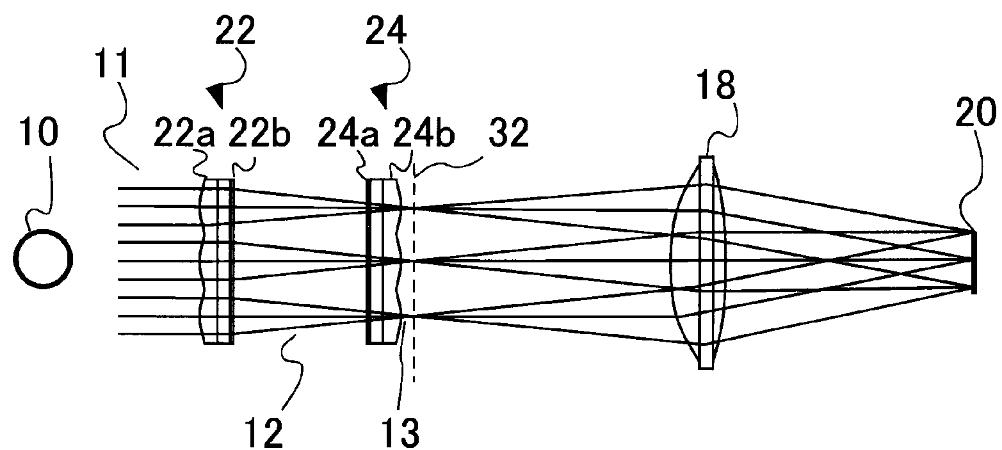
FIG.2B YZ plane
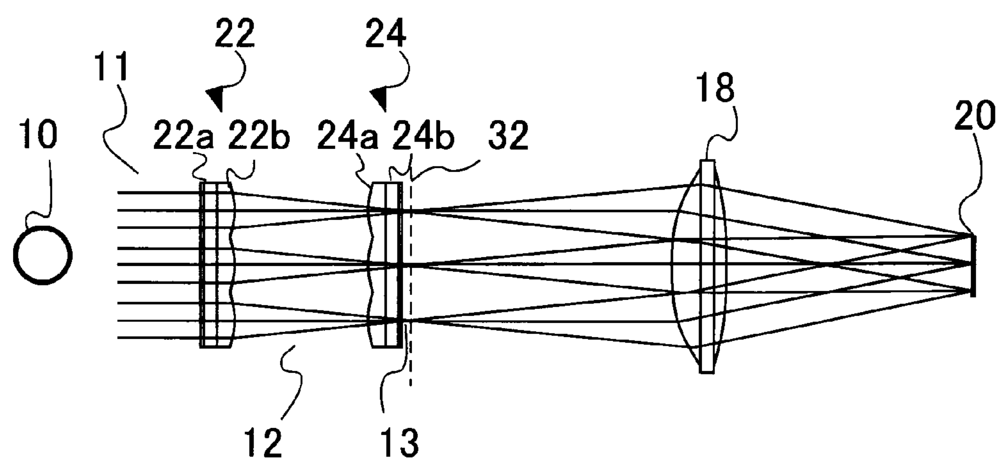

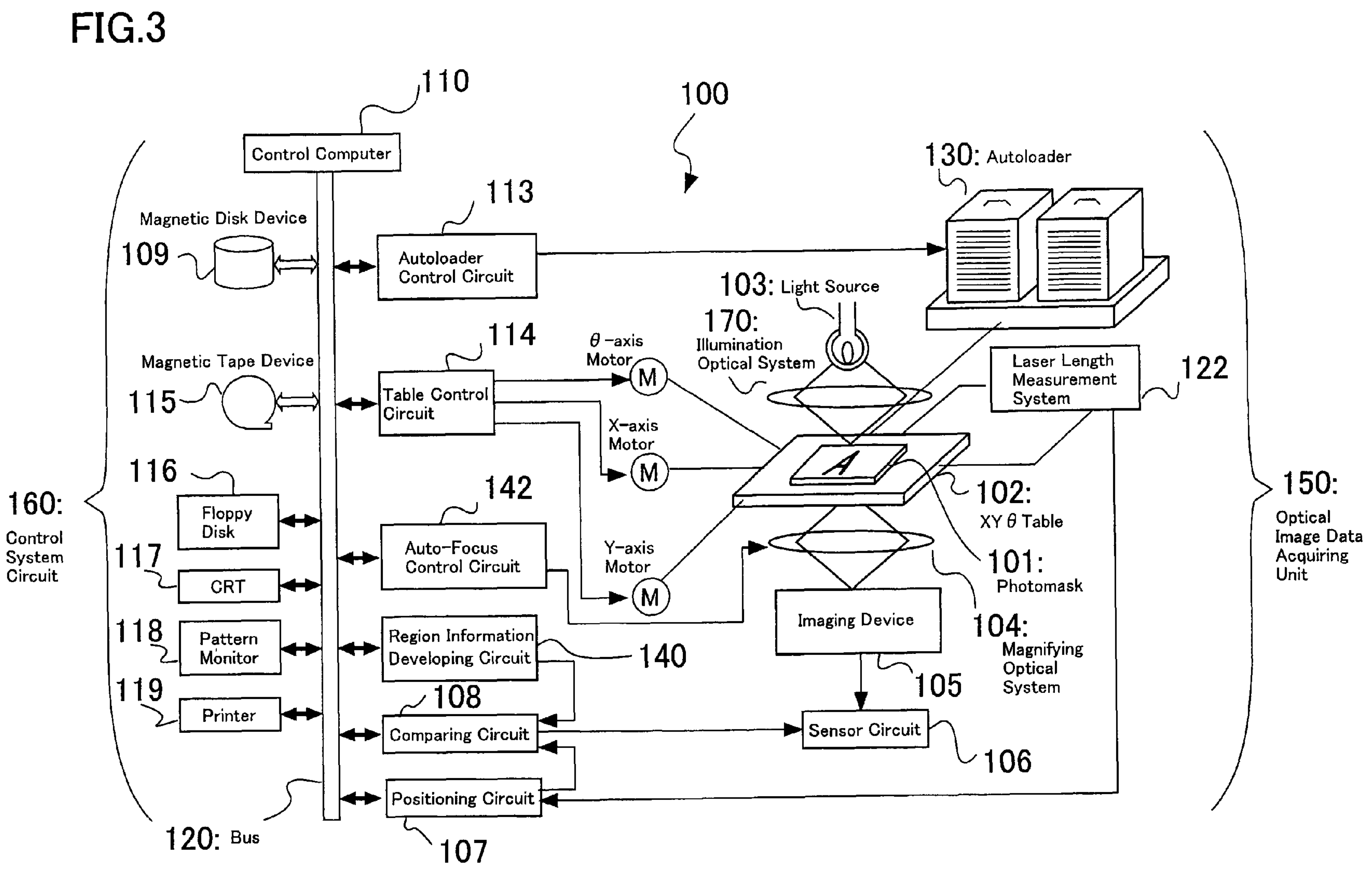
FIG.3
110
Control Computer
100
113
Autoloader Control Circuit
130: Autoloader
Magnetic Disk Device
109
103: Light Source
170: Illumination Optical System
114
Table Control Circuit
θ-axis Motor
X-axis Motor
Y-axis Motor
M
Magnetic Tape Device
115
Laser Length Measurement System
122
116
Floppy Disk
160: Control System Circuit
117
CRT
142
Auto-Focus Control Circuit
102: XY θ Table
101: Photomask
150: Optical Image Data Acquiring Unit
118
Pattern Monitor
Region Information Developing Circuit
140
Imaging Device
104: Magnifying Optical System
119
Printer
108
Comparing Circuit
105
Sensor Circuit
106
Positioning Circuit
107
120: Bus FIG.4A XZ plane RELATED ART
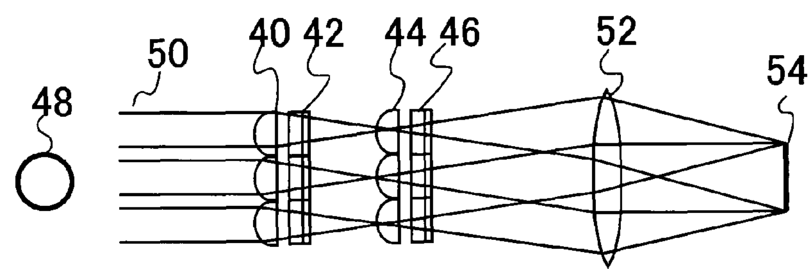
FIG.4B YZ plane
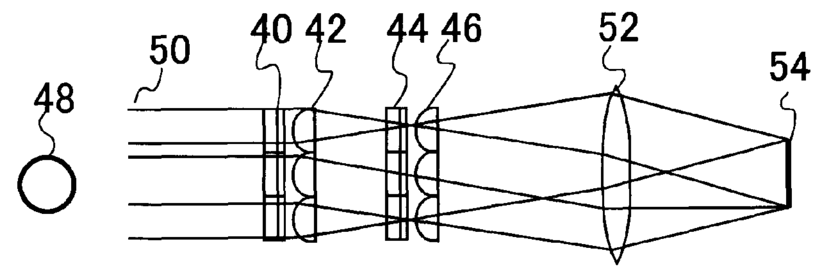

LIGHTING OPTICAL APPARATUS AND SAMPLE INSPECTION APPARATUS

CROSS-REFERENCE TO RELATED APPLICATION

This application is based upon and claims the benefit of priority from Japanese Patent Application No. 2007-090423, filed on Mar. 30, 2007, the entire contents of which are incorporated herein by reference.

FIELD OF THE INVENTION

The present invention relates to a lighting optical apparatus and a sample inspection apparatus using a deep ultraviolet light source.

BACKGROUND OF THE INVENTION

With an increase in integration degree of ICs in recent years, lighting optical apparatuses using deep ultraviolet light sources with shorter wavelengths are growing in importance. This is because making wavelengths of a light source in an exposure device of LSI or a sample inspection apparatus shorter generally leads to improved resolution. Moreover, a lighting optical apparatus needs to illuminate an irradiated plane with uniform illumination distribution and, for this purpose, an integrator optical system is known to be effective (for example, JP-A 2006-98156 (KOKAI)).

FIG. 4 exemplifies an integrator optical system of a conventional lighting optical apparatus. FIG. 4A is a sectional view on an XZ plane and FIG. 4B is a sectional view on a YZ plane. Cylindrical lenses 40 and 44 have a cylinder axis directed in the Y axis and thus have no curvature on the YZ plane. Cylindrical lenses 42 and 46, on the other hand, have a cylinder axis directed in the X axis and thus have no curvature on the XZ plane. A ray 50 emitted from a deep ultraviolet light source 48 and incident from the left side are split in the X direction by the cylindrical lens 40 and in the Y direction by the cylindrical lens 42. Such a plurality of split light fluxes is superimposed on an irradiated plane 54 by a condenser lens 52 to form uniform illumination distribution.

Here, the cylindrical lenses 44 and 46 assume a role of a field lens that aligns directions of a plurality of light fluxes that, after passing through the cylindrical lenses 40 and 42 respectively, are incident. If a ray whose component is not in parallel with the ray 50 incident on the cylindrical lenses 40 and 42 is partially mixed, some light fluxes whose direction is not aligned arise in the plurality of split light fluxes emitted from the cylindrical lenses 40 and 42. Thus, a problem arises that illumination distribution on the irradiated plane 54 becomes non-uniform. The problem is solved by the plurality of light fluxes being aligned by the field lens.

The present invention has been developed in view of the above circumstances and an object thereof is to provide a lighting optical apparatus and a sample inspection apparatus using a deep ultraviolet light source that provide high illuminant and highly uniform illuminant on an irradiated plane.

SUMMARY OF THE INVENTION

A lighting optical apparatus in an aspect of the present invention comprises a deep ultraviolet light source from which a deep ultraviolet ray is emitted; a first double-sided cylindrical lens on which the deep ultraviolet ray emitted from the deep ultraviolet light source is incident, from which the ray is emitted after being split into a plurality of first light fluxes, and which has a cylindrical lens array on both sides in a configuration in which cylinder axes intersect at right angles; a second double-sided cylindrical lens on which the plurality of first light fluxes emitted from the first double-sided cylindrical lens is incident, from which the fluxes are emitted after directions of the plurality of first light fluxes being aligned as a plurality of second light fluxes, and which has a cylindrical lens array on both sides in the configuration in which cylinder axes intersect at right angles; and a condenser lens on which the plurality of second light fluxes is incident to superimpose the plurality of second light fluxes.

A sample inspection apparatus in an aspect of the present invention comprises an illuminating optical system; a table on which a sample illuminated by the illuminating optical system is placed; an magnifying optical system for forming an image of the sample; and an imaging device for imaging the image of the sample, wherein a portion of the illuminating optical system is constituted by the lighting optical apparatus according to the above mentioned apparatus of the present invention.

BRIEF DESCRIPTION OF THE DRAWINGS

FIG. 1 is a diagram showing a configuration of a lighting optical apparatus in a first embodiment.

FIG. 2 is a diagram showing the configuration of a lighting optical apparatus in a second embodiment.

FIG. 3 is a schematic diagram showing the configuration of a sample inspection apparatus in a third embodiment.

FIG. 4 is a diagram showing the configuration of a conventional lighting optical apparatus.

DETAILED DESCRIPTION OF THE EMBODIMENTS

The inventors focused on an aspect that, in a conventional lighting apparatus as shown in FIG. 4, a lens is formed for each cylindrical array surface of a cylinder axis, leading to many components, that is, many adjustment elements. The inventors also focused on an aspect that transmittance drops sharply due to Fresnel reflection because a cylindrical lens alone has as many as eight glass boundary surfaces and the problem of Fresnel reflection could become a particularly serious problem generally in deep ultraviolet rays having a high Fresnel reflectance.

Further, in addition to the above problems, the inventors also regarded possible glass burning of a conventional lighting apparatus as a problem. In FIG. 4, the cylindrical lenses 40 and 42 condense light into the cylindrical lenses 44 and 46 respectively. If a deep ultraviolet ray has a relatively high absorptance in a glass, the glass of the cylindrical lens 44 or 46 could thereby be burnt, which is not preferable.

Embodiments of a lighting optical apparatus that solve the above problems, are easy to adjust due to a configuration with fewer components, and provide high illuminant and highly uniform illuminant on an irradiated plane will be described below with reference to drawings.

First Embodiment

A lighting optical apparatus in the first embodiment of the present invention comprises a deep ultraviolet light source from which a deep ultraviolet ray is emitted, and a first double-sided cylindrical lens on which the deep ultraviolet ray emitted from the deep ultraviolet light source is incident, from which the ray is emitted after being split into a plurality of first light fluxes, and which has a cylindrical lens array on both sides in the configuration in which cylinder axes intersect at right angles. Also, a second double-sided cylindrical lens on which the plurality of first light fluxes emitted from the first double-sided cylindrical lens is incident, from which the fluxes are emitted after directions of the plurality of first light fluxes being aligned as a plurality of second light fluxes, and which has a cylindrical lens array on both sides in the configuration in which cylinder axes intersect at right angles is provided. Further, a condenser lens on which the plurality of second light fluxes is incident to superimpose the plurality of second light fluxes is provided.

FIG. 1 shows a diagram showing a lighting optical apparatus in the present embodiment. FIG. 1A is a sectional view on the XZ plane and FIG. 1B is a sectional view on the YZ plane. First, the lighting optical apparatus in the present embodiment comprises a deep ultraviolet light source 10 from which a deep ultraviolet ray 11 is emitted. In addition, the lighting optical apparatus comprises a first double-sided cylindrical lens 14 that splits the deep ultraviolet ray 11 emitted from the deep ultraviolet light source 10 into a plurality of first light fluxes 12. By splitting the deep ultraviolet ray 11 into the plurality of first light fluxes 12, the first double-sided cylindrical lens 14 assumes the role of equalizing intensity non-uniformity inherent in the deep ultraviolet ray 11 on an irradiated surface 20.

A side of incidence 14*a* of the first double-sided cylindrical lens 14 is constituted by a cylindrical array having a cylinder axis directed in the Y direction and has no curvature on the YZ plane. In contrast, a side of emission 14*b* of the first double-sided cylindrical lens 14 is constituted by a cylindrical array having a cylinder axis directed in the X direction and has no curvature on the XZ plane. The first double-sided cylindrical lens 14 has in this way two cylindrical lens arrays, with each array on one side of the lens and cylinder axes intersecting at right angles.

Here, on the other side of the first double-sided cylindrical lens 14 opposite to the deep ultraviolet light source 10, a second double-sided cylindrical lens 16 on which the plurality of first light fluxes 12 emitted from the first double-sided cylindrical lens 14 is incident and from which, after directions of the plurality of first light fluxes 12 being aligned, these light fluxes are emitted as a plurality of second light fluxes is provided. If any ray of light having a component not in parallel is mixed in a ray of light incident on the first double-sided cylindrical lens 14, the second double-sided cylindrical lens 16 acts as a so-called field lens that assumes the role of equalizing illuminant non-uniformity caused on the irradiated surface 20 by correcting the direction thereof.

A side of incidence 16*a* of the double-sided cylindrical lens 16 is constituted by a cylindrical array having a cylinder axis directed in the Y direction and has no curvature on the YZ plane. In contrast, a side of emission 16*b* of the double-sided cylindrical lens 16 is constituted by a cylindrical array having a cylinder axis directed in the X direction and has no curvature on the XZ plane. Like the first double-sided cylindrical lens 14, the double-sided cylindrical lens 16 has in this way two cylindrical lens arrays, with each array on one side of the lens and cylinder axes intersecting at right angles.

Then, a condenser lens 18 on which a plurality of second light fluxes 13 emitted from the second double-sided cylindrical lens 16 after directions thereof being aligned is incident to superimpose the plurality of second light fluxes 13 on the irradiated surface 20.

Here, the deep ultraviolet ray 11 is incident from the deep ultraviolet light source 10 on the first double-sided cylindrical lens 14 from the side of incidence 14*a*. The deep ultraviolet ray 11 is split in the X direction by the cylindrical array of the side of incidence 14*a* and in the Y direction by the cylindrical array of the side of emission 14*b*. The plurality of split first light fluxes 12 is emitted and condensed on a luminescent spot surface 22 as the plurality of second light fluxes 13 after passing through the second double-sided cylindrical lens 16. Here, in the second double-sided cylindrical lens 16, a portion of light fluxes whose direction is not aligned among light fluxes emitted from the first double-sided cylindrical lens 14 is aligned with the direction of the overall light fluxes to produce the plurality of second light fluxes. Further, light condensed on the luminescent spot surface 22 is superimposed on the irradiated surface 20 by the condenser lens to have highly uniform illuminance distribution.

In a light optical apparatus in the present invention, as described above, a cylindrical lens having a cylindrical lens array surface on both sides with cylinder axes intersecting at right angles is used in order to achieve highly uniform illuminant distribution on an irradiated surface. An optical part that conventionally requires four lenses can thereby be constituted by two lenses so that two components, that is, two adjustment elements can be reduced. Therefore, lighting optical apparatuses with high productivity can be provided because adjustments are made easier. In addition, Fresnel reflection is reduced and thus, lighting optical apparatuses having improved illuminant on an irradiated surface can be provided.

In the present embodiment, it is preferable that a first double-sided cylindrical lens be close to a focal point of a second double-sided cylindrical lens on the side of the first double-sided cylindrical lens. In other words, as shown in FIG. 1, it is preferable that the first double-sided cylindrical lens 14 be at a focal point (object focal point) of the second double-sided cylindrical lens 16 on the side of the first double-sided cylindrical lens 14, that is, approximately a focal length f2 of the second double-sided cylindrical lens 16 from the second double-sided cylindrical lens 16 on the side of the deep ultraviolet light source 10. This is intended to cause the second double-sided cylindrical lens 16 to act as a field lens most effectively.

Also in the present embodiment, as shown in FIG. 1, it is preferable that the second double-sided cylindrical lens 16 be arranged on the side of the first double-sided cylindrical lens 14 from a focal point (back focal point) of the first double-sided cylindrical lens 14 on the side of the second double-sided cylindrical lens 16. That is, it is preferable that the second double-sided cylindrical lens 16 be on the side of the first double-sided cylindrical lens 14 from the position a focal length f1 of the first double-sided cylindrical lens 14 apart from the first double-sided cylindrical lens 14 to the side of the condenser lens, in other words, from the luminescent spot surface 22 where the deep ultraviolet ray 11 is condensed. By shifting the position where the deep ultraviolet ray 11 is condensed from that of the second double-sided cylindrical lens 16, which acts as a field lens to prevent condensing in the lens from occurring, as described above, it becomes possible to prevent the lenses of the second double-sided cylindrical lens 16 from being burnt. Here, the present invention does not exclude a configuration in which the second double-sided cylindrical lens 16 is positioned on the side of the condenser lens 18 from the luminescent spot surface 22. However, this configuration makes the curvature of the first double-sided cylindrical lens 14 relatively larger and thus, is not preferable due to a concern about an increase in aberration.

Also in the present embodiment, as shown in FIG. 1, it is preferable that the focal point (back focal point) of each cylinder axis on the side of the condenser lens of an optical system combining the first double-sided cylindrical lens 14 and second double-sided cylindrical lens 16, that is, a set of luminescent spots (or a group of focal points) condensed by the combined optical system is on the same plane. This is because uniformity of illuminant distribution on the irradiated surface 20 is improved compared with a case in which the luminescent spot surface 22 is curved or uneven.

Also in the present embodiment, as shown in FIG. 1, it is preferable that the focal point (object focal point) of the condenser lens 18 on the side of the second double-sided cylindrical lens 16, that is, the position a focal point f3 apart from the condenser lens 18 to the side of the deep ultraviolet light source 10 (front side) be on a plane where the focal point (back focal point) of each cylinder axis on the side of the condenser lens of the optical system combining the first double-sided cylindrical lens 14 and second double-sided cylindrical lens 16 exists. By satisfying this condition, each light flux traveling to the irradiated surface will be parallel, making management of the angle of incidence of light fluxes easier.

Conditions described above as a preferable embodiment, that is, the configuration shown in FIG. 1 can be achieved if the radius of curvature of each cylindrical array satisfies conditions shown below.

If the radius of curvature of one element, that is, one cylinder of the cylindrical lens array on the side of incidence 14*a* of the first double-sided cylindrical lens 14 is R1, that of one element of the cylindrical lens array on the side of emission 14*b* of the first double-sided cylindrical lens is R2, that of one element of the cylindrical lens array on the side of incidence 16*a* of the second double-sided cylindrical lens 16 is R3, and that of one element of the cylindrical lens array on the side of emission 16*b* of the second double-sided cylindrical lens 16 is R4, by satisfying relationships shown below $$R3<R2<R1 \text{ and } R3\leqq R4<R1$$

the above preferable configuration can be achieved.

This is evident from a relationship between the curvature and principal plane of a lens having finite thickness and has been confirmed by optical simulations.

In the above relationships, it is particularly preferable that a relationship R2=R4 be satisfied. This is because productivity of productivity lenses is better if the types of curvature of lens are fewer and performance of illumination changes less by setting the condition R2=R4.

Also, it is particularly preferable that a relationship R3=R4<R2<R1 be satisfied. By satisfying this condition, illuminant and illuminant uniformity on the irradiated surface will further be improved.

According to the present embodiment described above, it becomes possible to provide a lighting optical apparatus that is easy to adjust due to a configuration with fewer components, has high illuminant and highly uniform illuminant on an irradiated surface, and uses a deep ultraviolet light source that is unlikely to cause lens burning.

Second Embodiment

A lighting optical apparatus in the second embodiment of the present invention is the same as that in the first embodiment except that the cylinder axis of the cylindrical lens array of the first double-sided cylindrical lens and that of the cylindrical lens array of the second double-sided cylindrical lens are perpendicular to each other, instead of being parallel, and thus a duplicated description is omitted.

FIG. 2 shows a lighting optical apparatus in the present embodiment. FIG. 2A is a sectional view on the XZ plane and FIG. 2B is a sectional view on the YZ plane.

In contrast to the first embodiment, as shown in FIG. 2, the cylinder axis of a side of incidence 22*a* of a first double-sided cylindrical lens 22 and the cylinder axis of a side of incidence 24*a* of a second double-sided cylindrical lens 24 are configured so that they are perpendicular to each other, that is, they intersect at right angles. Also, the cylinder axis of a side of emission 22*b* of a first double-sided cylindrical lens 22 and the cylinder axis of a side of emission 24*b* of a second double-sided cylindrical lens 24 are configured so that they are perpendicular to each other, that is, they intersect at right angles.

In the present embodiment, a luminescent spot surface 32 tends to come closer to the second double-sided cylindrical lens 24 due to the configuration thereof compared with that of the first embodiment. Therefore, a concern about lens burning will be greater in comparison with the first embodiment. However, otherwise, operations and effects similar to those of the first embodiments can be implemented.

Third Embodiment

A sample inspection apparatus in the third embodiment of the present invention comprises an illuminating optical system, a table on which a sample illuminated by the illuminating optical system is placed, an magnifying optical system for forming a sample image, and an imaging device for imaging a sample image, and a portion of the illuminating optical system is constituted by a lighting optical apparatus in the first embodiment.

FIG. 3 is a conceptual diagram showing the configuration of a sample inspection apparatus in the present embodiment. In FIG. 3, a sample inspection apparatus 100 for checking for defects of a sample such as a mask and a substrate including a wafer comprises an optical image data acquisition part 150 and a control system circuit 160. The optical image data acquiring unit 150 comprises an illumination optical system 170 including a deep ultraviolet light source 103, an XYθ table 102 on which a sample illuminated by the illumination optical system 170 is placed, an magnifying optical system 104 for forming a sample image, and an imaging device 105 for imaging a sample image, for example, a photodiode array. Further, the optical image data acquiring unit 150 comprises a sensor circuit 106, a laser length measurement system 122, and an auto-loader 130. In the control system circuit 160, a control computer 110 to act as a computer is connected to a positioning circuit 107, a comparing circuit 108, which is an example of a comparing part, an region information developing circuit 140, which is an example of an area image data generator, an auto-loader control circuit 113, a table control circuit 114, an auto-focus control circuit 142, a magnetic disk device 109, which is an example of a magnetic apparatus, a magnetic tape device 115, a floppy (registered trademark) disk 116, a CRT 117, a pattern monitor 118, and a printer 119 via a bus 120 to be a data transmission line. The XYθ table 102 is driven by an X-axis motor, a Y-axis motor, and a θ-axis motor. In FIG. 3, components other than those necessary for describing the present embodiment are omitted. Other components normally needed for the sample inspection apparatus 100 are naturally included.

Here, a portion of the illumination optical system 170 is constituted by a lighting optical apparatus in the first embodiment. Details thereof has been described in the first embodiment and thus, a duplicated description is omitted.

According to the present embodiment, a sample inspection apparatus using a deep ultraviolet light source with a lighting optical apparatus that is easy to adjust due to a configuration with fewer components and has high illuminant and highly uniform illuminant on an irradiated surface, can be provided.

Therefore, a sample inspection apparatus in the present embodiment has superior operations and effects that maintenance is easy, the operating ratio is improved because the frequency of replacement can be lowered, and inspection accuracy is high because illuminant and illuminant uniformity on an irradiated surface are improved.

Embodiments of the present invention have been described above with reference to concrete examples. Though a description of components that are not directly needed for describing the present invention such as a lighting optical apparatus and a sample inspection apparatus is omitted in descriptions of embodiments, components needed for a lighting optical apparatus or a sample inspection apparatus can suitably be selected and used.

In addition, all lighting optical apparatuses and sample inspection apparatuses having components of the present invention and whose design can suitably be modified by a person skilled in the art are included in the scope of the present invention. Additional advantages and modification will readily occur to those skilled in the art.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A lighting optical apparatus, comprising:

a deep ultraviolet light source from which a deep ultraviolet ray is emitted;

a first double-sided cylindrical lens on which the deep ultraviolet ray emitted from the deep ultraviolet light source is incident, from which the ray is emitted after being split into a plurality of first light fluxes, and which includes a cylindrical lens array on both sides in a configuration in which cylinder axes intersect at right angles;

a second double-sided cylindrical lens on which the plurality of first light fluxes emitted from the first double-sided cylindrical lens is incident, from which the fluxes are emitted after directions of the plurality of first light fluxes are aligned as a plurality of second light fluxes, and which includes a cylindrical lens array on both sides in the configuration in which cylinder axes intersect at right angles; and a condenser lens on which the plurality of second light fluxes is incident to superimpose the plurality of second light fluxes, wherein the cylinder axis of the cylindrical lens array on a side of incidence of the first double-sided cylindrical lens and that of the cylindrical lens array on the side of incidence of the second double-sided cylindrical lens are perpendicular.

2. A lighting optical apparatus, comprising:

a deep ultraviolet light source from which a deep ultraviolet ray is emitted;

a first double-sided cylindrical lens on which the deep ultraviolet ray emitted from the deep ultraviolet light source is incident, from which the ray is emitted after being split into a plurality of first light fluxes, and which includes a cylindrical lens array on both sides in a configuration in which cylinder axes intersect at right angles;

a second double-sided cylindrical lens on which the plurality of first light fluxes emitted from the first double-sided cylindrical lens is incident, from which the fluxes are emitted after directions of the plurality of first light fluxes are aligned as a plurality of second light fluxes, and which includes has a cylindrical lens array on both sides in the configuration in which cylinder axes intersect at right angles; and a condenser lens on which the plurality of second light fluxes is incident to superimpose the plurality of second light fluxes, wherein if a radius of curvature of one element of the cylindrical lens array on a side of incidence of the first double-sided cylindrical lens is R1, that of one element of the cylindrical lens array on the side of emission of the first double-sided cylindrical lens is R2, that of one element of the cylindrical lens array on the side of incidence of the second double-sided cylindrical lens is R3, and that of one element of the cylindrical lens array on the side of emission of the second double-sided cylindrical lens is R4, a relationship of $$R3<R2=R4<R1$$

is satisfied.

3. A lighting optical apparatus, comprising:

a deep ultraviolet light source from which a deep ultraviolet ray is emitted;

a first double-sided cylindrical lens on which the deep ultraviolet ray emitted from the deep ultraviolet light source is incident, from which the ray is emitted after being split into a plurality of first light fluxes, and which includes a cylindrical lens array on both sides in a configuration in which cylinder axes intersect at right angles;

a second double-sided cylindrical lens on which the plurality of first light fluxes emitted from the first double-sided cylindrical lens is incident, from which the fluxes are emitted after directions of the plurality of first light fluxes are aligned as a plurality of second light fluxes, and which includes a cylindrical lens array on both sides in the configuration in which cylinder axes intersect at right angles; and a condenser lens on which the plurality of second light fluxes is incident to superimpose the plurality of second light fluxes, wherein the cylinder axis of the cylindrical lens array on a side of incidence of the first double-sided cylindrical lens and that of the cylindrical lens array on the side of incidence of the second double-sided cylindrical lens are parallel, wherein if a radius of curvature of one element of the cylindrical lens array on a side of incidence of the first double-sided cylindrical lens is R1, that of one element of the cylindrical lens array on the side of emission of the first double-sided cylindrical lens is R2, that of one element of the cylindrical lens array on the side of incidence of the second double-sided cylindrical lens is R3, and that of one element of the cylindrical lens array on the side of emission of the second double-sided cylindrical lens is R4, a relationship of $$R3<R2=R4<R1$$

is satisfied.

4. A lighting optical apparatus, comprising:

a deep ultraviolet light source from which a deep ultraviolet ray is emitted;

a first double-sided cylindrical lens on which the deep ultraviolet ray emitted from the deep ultraviolet light source is incident, from which the ray is emitted after being split into a plurality of first light fluxes, and which includes a cylindrical lens array on both sides in a configuration in which cylinder axes intersect at right angles;

a second double-sided cylindrical lens on which the plurality of first light fluxes emitted from the first double-sided cylindrical lens is incident, from which the fluxes are emitted after directions of the plurality of first light fluxes are aligned as a plurality of second light fluxes, and which includes a cylindrical lens array on both sides in the configuration in which cylinder axes intersect at right angles; and a condenser lens on which the plurality of second light fluxes is incident to superimpose the plurality of second light fluxes, wherein if a radius of curvature of one element of the cylindrical lens array on a side of incidence of the first double-sided cylindrical lens is R1, that of one element of the cylindrical lens array on the side of emission of the first double-sided cylindrical lens is R2, that of one element of the cylindrical lens array on the side of incidence of the second double-sided cylindrical lens is R3, and that of one element of the cylindrical lens array on the side of emission of the second double-sided cylindrical lens is R4, a relationship of $$R3=R4<R2<R1$$

is satisfied.

5. A lighting optical apparatus, comprising:

a deep ultraviolet light source from which a deep ultraviolet ray is emitted;

a first double-sided cylindrical lens on which the deep ultraviolet ray emitted from the deep ultraviolet light source is incident, from which the ray is emitted after being split into a plurality of first light fluxes, and which includes a cylindrical lens array on both sides in a configuration in which cylinder axes intersect at right angles;

a second double-sided cylindrical lens on which the plurality of first light fluxes emitted from the first double-sided cylindrical lens is incident, from which the fluxes are emitted after directions of the plurality of first light fluxes are aligned as a plurality of second light fluxes, and which includes a cylindrical lens array on both sides in the configuration in which cylinder axes intersect at right angles; and a condenser lens on which the plurality of second light fluxes is incident to superimpose the plurality of second light fluxes, wherein the cylinder axis of the cylindrical lens array on a side of incidence of the first double-sided cylindrical lens and that of the cylindrical lens array on the side of incidence of the second double-sided cylindrical lens are parallel, wherein if a radius of curvature of one element of the cylindrical lens array on a side of of incidence of the first double-sided cylindrical lens is R1, that of one element of the cylindrical lens array on the side of emission of the first double-sided cylindrical lens is R2, that of one element of the cylindrical lens array on the side of incidence of the second double-sided cylindrical lens is R3, and that of one element of the cylindrical lens array on the side of emission of the second double-sided cylindrical lens is R4, a relationship of $$R3=R4<R2<R1$$

is satisfied.

* * * * *